US00PP30888P3

(12) United States Plant Patent
Kapac

(10) Patent No.: US PP30,888 P3
(45) Date of Patent: Sep. 24, 2019

(54) ***RUGOSA* SHRUB ROSE PLANT NAMED 'KAPSWEHP'**

(50) Latin Name: *Rosa rugosa*
Varietal Denomination: KAPswehp

(71) Applicant: Gardens Alive! Inc., Lawrenceburg, IN (US)

(72) Inventor: Jay Kapac, Castaic, CA (US)

(73) Assignee: Gardens Alive! Inc., Lawrenceburg, IN (US)

( * ) Notice: Subject to any disclaimer, the term of this patent is extended or adjusted under 35 U.S.C. 154(b) by 0 days.

(21) Appl. No.: 15/732,114

(22) Filed: Sep. 19, 2017

(65) Prior Publication Data

US 2019/0090395 P1 Mar. 21, 2019

(51) Int. Cl.
*A01H 5/02* (2018.01)
*A01H 6/74* (2018.01)

(52) U.S. Cl.
USPC ..... Plt./102
CPC ..... *A01H 6/749* (2018.05)

(58) Field of Classification Search
USPC ..... Plt./102
CPC ..... A01H 6/749; A01H 5/02
See application file for complete search history.

(56) References Cited

U.S. PATENT DOCUMENTS

PP12,055 P2 8/2001 Zary

*Primary Examiner* — Keith O. Robinson
(74) *Attorney, Agent, or Firm* — McKee, Voorhees & Sease, PLC

(57) ABSTRACT

A new variety of *Rugosa* rose suitable garden decoration, having flowers of pink coloration and production on many edible hips.

4 Drawing Sheets

Classification: The present invention relates to a new *Rosa rugosa* plant.

Variety denomination: The new plant has the varietal denomination 'KAPswehp'.

BACKGROUND OF THE INVENTION

This invention relates to a new and distinct variety of *Rugosa* Rose. It has as its seed parent a variety known as "Niven's White' *Rugosa*' (not patented), and as its pollen parent an unknown *Rugosa* rose. It was hybridized by Jay Kapac.

SUMMARY OF THE INVENTION

Among the features which distinguish the new variety from others presently available and commercial rose cultivars known to the inventor are the following combinations of characteristics:

1. Repeat flowering throughout the growing season even with a heavy fruit load.
2. Production of large sweet hips suitable for fresh eating or for processing.
3. Resistance against all common rose diseases found in the United States.
4. Cold hardy with no freeze damage when tested down to −20 degrees F.
5. Fragrant. The flower has a strong spicy clove scent.

This unique combination of characteristics makes this plant suitable for outdoor garden decoration.

Asexual reproduction of the new variety by budding and softwood propagation, as performed in Kern County, Calif. and Tipp City, Ohio shows that the foregoing and other distinguishing characteristics come true to form and are established and transmitted through succeeding asexual propagations. 'KAPswehp' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, "Niven's White' *Rugosa*' by the following combination of characteristics: Its flower color is N78B to N78C while 'Niven's White' is the palest pink at close to N155B. 'KAPswehp' is a very vigorous plant growing quickly to 5-6' tall in Ohio within the first two years after planting. 'Niven's White' is slower to establish and shorter in growth. Hips are produced on both plants but 'KAPswehp' produces larger hips with thicker flesh and sweet taste.

The new variety cannot be distinguished from its pollen parent because it is not known with sufficient accuracy.

COMPARISON WITH THE CLOSEST COMMERCIALLY AVAILABLE CULTIVAR

The new variety may be distinguished from its closest commercially available cultivar, 'JACrulav' (U.S. Plant Pat. No. 12,055) by the following combination of characteristics: 'KAPswehp' grows to 60-72" in height while 'JACrulav' grows to 36-48" in height. 'JACrulav' also produces hips but they are much less sweet, smaller in size and have thinner flesh than 'KAPswehp.'

BRIEF DESCRIPTION OF ILLUSTRATIONS

The accompanying photographs illustrate the new variety and show the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

FIG. 1 depicts the new variety 'KAPswehp,' in particular the flowering thereof from bud to full bloom. The flowering variety was collected in June.

FIG. 2 depicts a rose bush of the new variety 'KAPswehp,' and represents the branches which provided the materials for FIG. 1. The plant of the new variety is a 3 to 4-year-old rose plant grown outdoors in Tipp City, Ohio.

FIG. 3 depicts fruit from the new variety 'KAPswehp' harvested from the rose bush depicted in FIG. 2.

FIG. 4 depicts fruit from the new variety 'KAPswehp' as attached to the rose bush.

DESCRIPTION OF THE NEW VARIETY

The following description is of 3 to 4-year-old rose plants of the new variety grown outdoors in Tipp City, Ohio in the month of June. Phenotypic expression may vary with environmental, cultural and climatic conditions, as well as differences in conditions of light and soil.

FLOWER

The new variety usually bears its flowers in small clusters of 3 or 5 flowers per stem. The clusters are pyramidal in shape. The profile of the lower portion of the flower is concave. Flowers are borne on strong medium to long stems 30-40 cm in length and 8-10 mm in diameter. Outdoors, the plant blooms abundantly and nearly continuously during the growing season. The flowers have a strong spicy clove fragrance.

BUD

The peduncle is about 3 to about 4 cm. in length, of average caliper (about 3 mm. in diameter), and stiff. It is pubescent having a few glands near the receptacle. Peduncle color is between 147C and 147D.

Before the calyx breaks, the bud is about 1.7 to about 2.0 cm. in diameter at the widest point, about 2.3 to about 2.5 cm. in length, and long pointed ovoid in shape. The surface of the bud bears several foliaceous appendages, several stipitate glands and glandular bloom, usually with slender foliaceous parts extending beyond the tip of the bud about ⅓ or more of its length. Bud color before flower color can be seen is between 146C and 146D.

The sepals are about 35 to about 45 mm. long and 8 mm. wide at the widest point. The outer surface color of the sepal is between 146C and 146D. Sepal extensions are medium. The outer surface of the sepal is moderately rough and bears one long foliaceous appendage with some stipitate glands, hairs and glandular bloom. The inner surface color of the sepal is near 147C. The inner surface of the sepal is covered with fine wooly tomentum; sepal margins are lined with many glands and numerous hairs.

The receptacle of the flower is medium in size (about 8 mm. in length and about 10 mm. in diameter). The receptacle is globular shaped in form. Its surface is smooth with an occasional gland and with fleshy walls. The receptacle color is between 146A and 146B.

As the petals open (after the calyx breaks), the bud is about 3.0 to 3.5 cm. long and about 5.0 cm. in diameter at widest point and pointed to ovoid in form. The color of the under surfaces of the newly opened petals is N78D at the petal base changing to N78C over the rest of the petal. At the point where the petal attaches, there is a small zone between 1C and 1D. The color of the upper surfaces of the newly opened petals is between N78B and N78C.

BLOOM

When fully open, the bloom ranges from about 7-8 cm. in diameter with the largest flowers expressed under cool night/warm day temperature. Petalage is single with about 5 petals under normal conditions. When partially open, the bloom form is cupped. When fully open, the bloom form flattens somewhat leaving the flower as a shallow cup.

PETALS

The substance of the petals is medium and of average thickness, with upper surfaces slightly shiny and under surfaces matte. The petals are about 4.5 to about 5.0 cm. in length and about 5.0 to about 5.5 cm. in width at the widest point. Petal margins are entire.

The outer petals are orbicular in shape with apices rounded and rarely notched.

The inner petals are oval to obovate in shape with apices rounded and rarely notched.

Petaloids have not been observed.

NEWLY OPENED FLOWER

The under-surface color of the outer petals is N78D at the base. Toward the middle of the petal is N78C. At the point where the petal attaches, there is a small zone of 1C to 1D averaging in size of 0.5 cm. by 1 cm. The upper surface color of the outer petals is between N78B and N78C. At the point where the petal attaches, there is a small zone of between 1C and 1D.

The general tonality of the newly opened flower is between N78B to N78C.

THREE-DAY-OLD FLOWER

The upper surface color of the outer petals N78B. At the point where the petal attaches, there is a small zone of between 1C and 1D. The under-surface color of the outer petals is between N78C to N78D. At the point where the petal attaches, there is small zone of near 1C to 1D.

The general tonality of the three-day-old flower is N78B and N78C.

On the spent bloom, the petals often drop off cleanly.

In June in Tipp City, Ohio, blooms on the bush growing outdoors generally last about 3 to 4 days. Cut roses from plants grown outdoors and kept at normal indoor living temperatures generally last about 4 to 5 days.

MALE REPRODUCTIVE ORGANS

Stamens are many in number averaging about 200 to 220 in number and are arranged regularly about the pistils. The filaments are medium length (about 6-7 mm.) most with anthers. Filaments are between 158C to 158D in color. The anthers are medium for the class and all open approximately at the same time. Anther color when immature is near 158B on the external part and near 158B on the internal part. Anther color at maturity is near 165C on the external part and near 177B on the internal part. Pollen is moderate to abundant and near 165C in color.

FEMALE REPRODUCTIVE ORGANS

Pistils vary in number (average about 60). The styles are moderately even, average in length (about 1 mm.), moderately heavy in caliper, and bunched. Stigma color is between 160C and 160D. Style color is near to 160D in color. Ovaries are enclosed in the calyx.

Hips are present on this variety in large numbers when grown in Tipp City, Ohio and in Wasco, Calif. Hips range from 2-3 cm in diameter with thick fleshy walls. Color ripens to 31B when mature and finishes close 43R when over ripe and ready to begin drying. Hips contain from 8-15 seed and are 4-5 mm long and 2-3 mm wide. Ripe seed color is 13D. Hips are sweet and slightly acidic in taste when fresh. They make a very good rose hip tea and when steamed, express a flavorful juice that can be made into a very fine tasting rose hip jelly.

FOLIAGE

The compound leaves are usually comprised of seven to nine leaflets and are borne abundantly. The mature leaves are about 15 cm. in length and about 13 cm in width at the widest point, leathery and very rugose in texture, and somewhat glossy in finish on the upper side and matte on the underside. The leaves have a reticulate venation pattern. The terminal leaflets are about 6.0 to 6.5 cm. in length and about 4.5 to 5.0 cm. in width at the widest point, shaped ovate with mostly acute to subacute apices and rounded bases. Their margins are simply serrate.

The upper surface color of the mature leaf is 146A. The under-surface color of the mature leaf is 148B. The under and upper colors of the leaf veins on the mature leaf are similar in coloration to the upper and under surfaces colors of the mature leaf. The upper surface color of the young leaf is between 146C and 146D. The under-surface color of the young leaf is 148C. The under and upper colors of the leaf veins on the young leaf are similar in coloration to the upper and under surfaces colors of the young leaf.

The rachis is average in caliper and smooth. The upper side is grooved with fine hairs all along the edges of the grove. The underside of the rachis is somewhat rough with small prickles present. The rachis color is near 148D on the underside and near 148C on the upper side. The stipules are about 25 to 28 mm. in length and about 10 mm. in width with points that usually turn out at an angle of more than 45 degrees. The under and upper surface color of the stipule is between 148C and 148D.

The petiole is average in caliper and smooth. The upper side is rounded. The underside of the petiole is smooth. The petiole is about 3 to about 4 mm. in length and about 1 to about 2 mm. in width at the widest point. The petiole color is near 148C on the underside and near 148C on the upper side.

The plant displays an average above well above average degree of resistance to powdery mildew (*Sphaerotheca pannosa* var. *rosae*), black spot (*Diplocarpon rosae*), rust (*Phragmidium mucronatum*) as compared to other commercial varieties grown under comparable conditions in Tipp City, Ohio and Wasco, Calif. The plant is completely winter hardy in Tipp City, Ohio.

GROWTH

The plant has a bushy upright growth habit (about 160 cm to about 190 cm. in height and about 120 to about 150 cm. spread at the widest point), with full branching. It displays vigorous growth and the canes are of medium caliper for the class (about 1 to 1.2 cm. in diameter at the widest point).

The color of the major stems is between 146C to 146D. They bear many moderate sized prickles that are about 4 to about 9 mm. in length. The large prickles are straight with a medium length base; prickle color is near 146C. The major stem bears many small prickles of similar shape and coloration and which are near 146C in color.

The color of the mature two-year-old branches is between 200A and 200B. They bear several large prickles which are of similar size and shape to the large prickles on the major stems; prickle color is near 199B. The branches have a few small prickles of similar shape and coloration and which are near 199B in color.

The color of the new shoots is near 147C but quickly changing to 146C. They bear several large prickles which are of similar size and shape to the large prickles on the major stems; prickle color is near 146C. The shoots bear many prickles of similar shape and coloration and which are near 146C in color. New shoots when exposed to full sun are near 147C as there is no anthocyanin present.

The invention claimed is:

1. A new and distinct *Rugosa* rose plant of the variety substantially as described and illustrated herein.

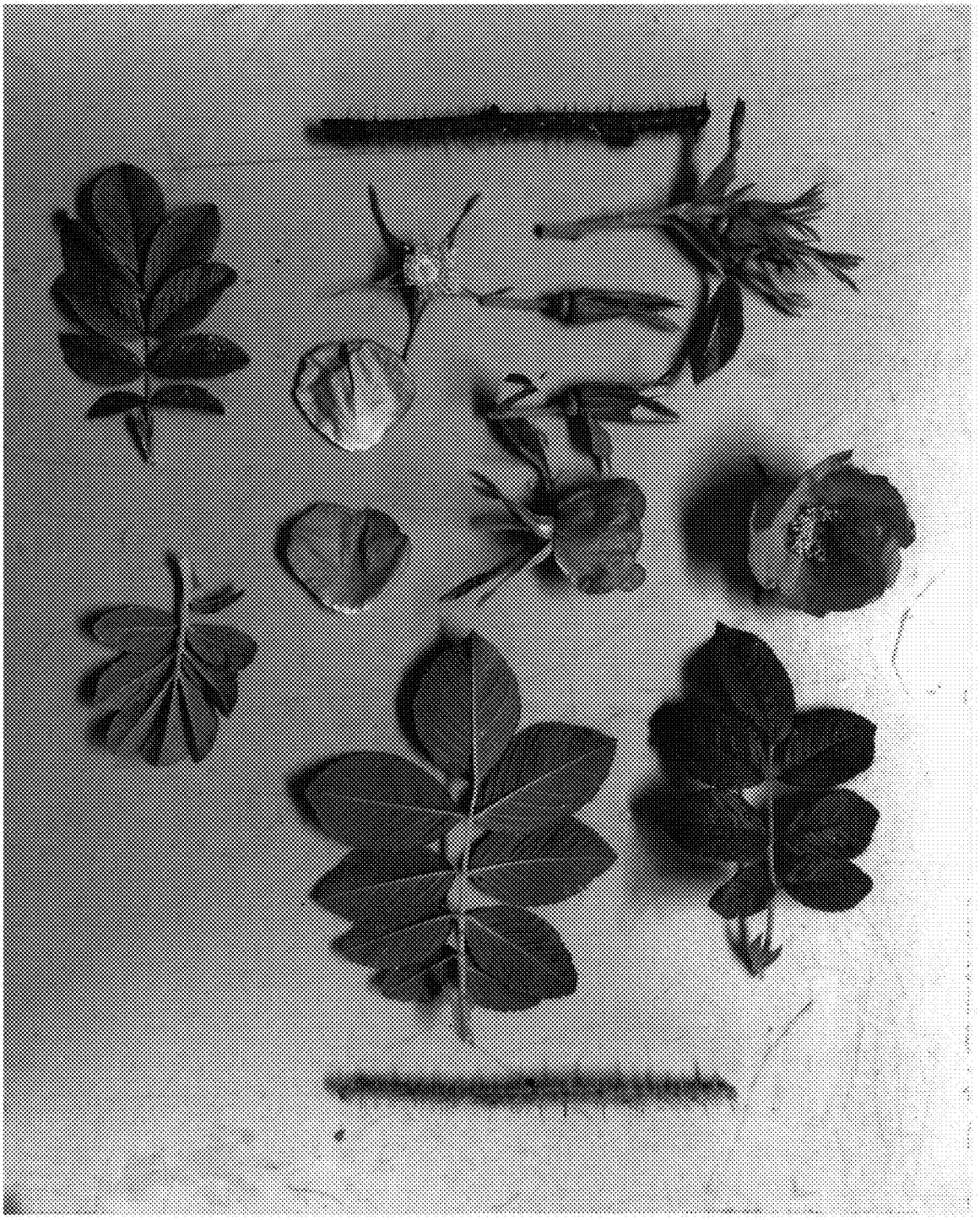

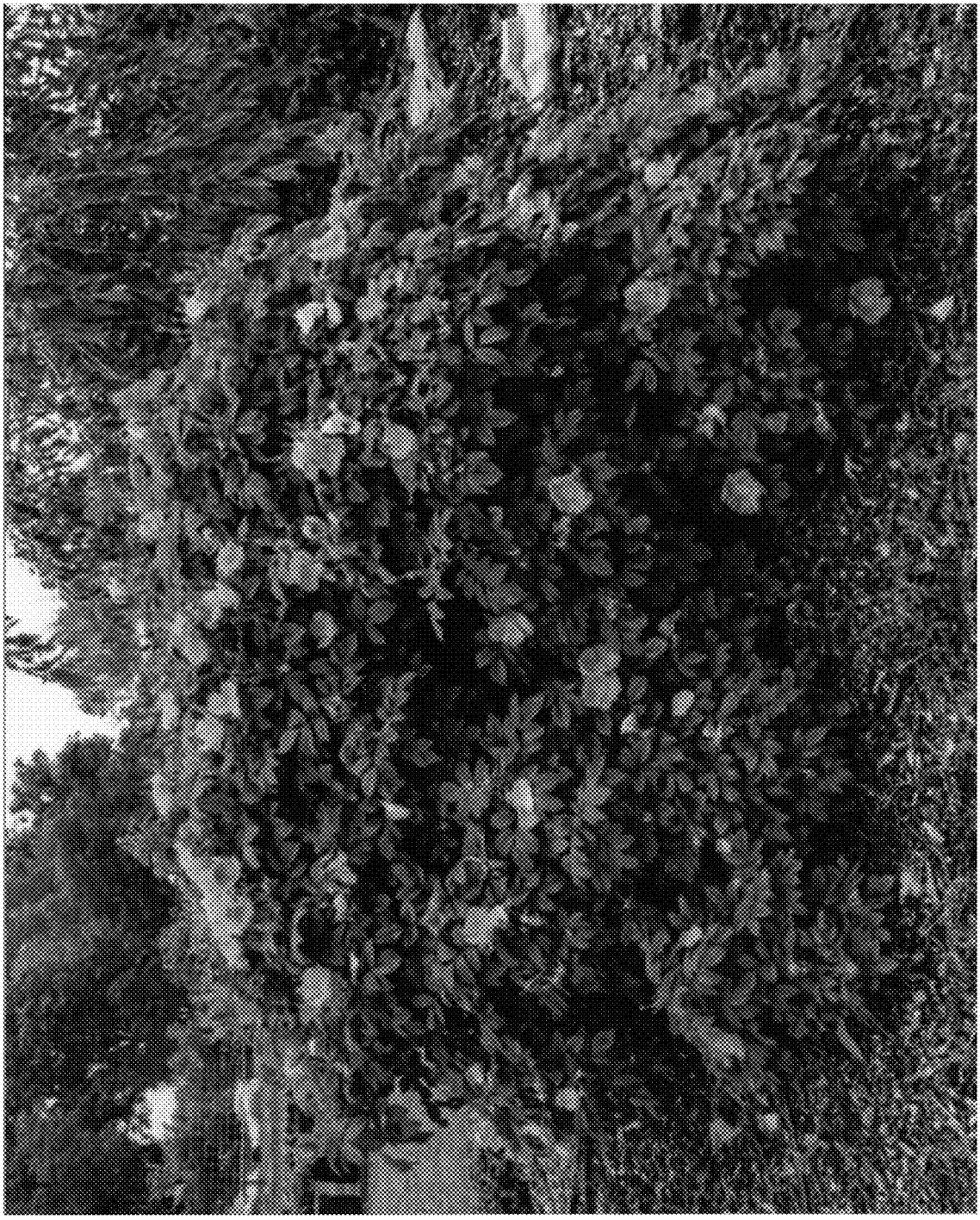

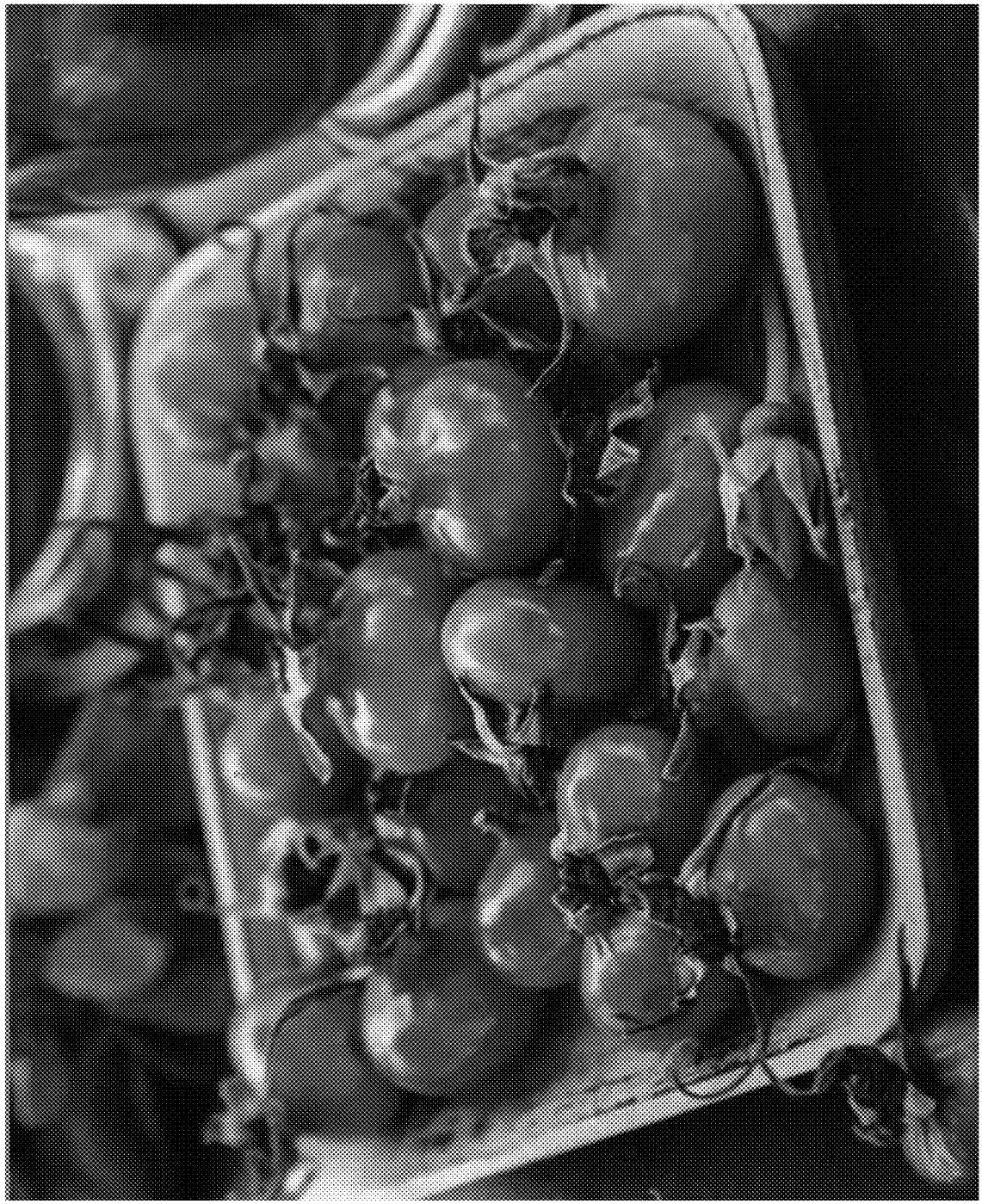

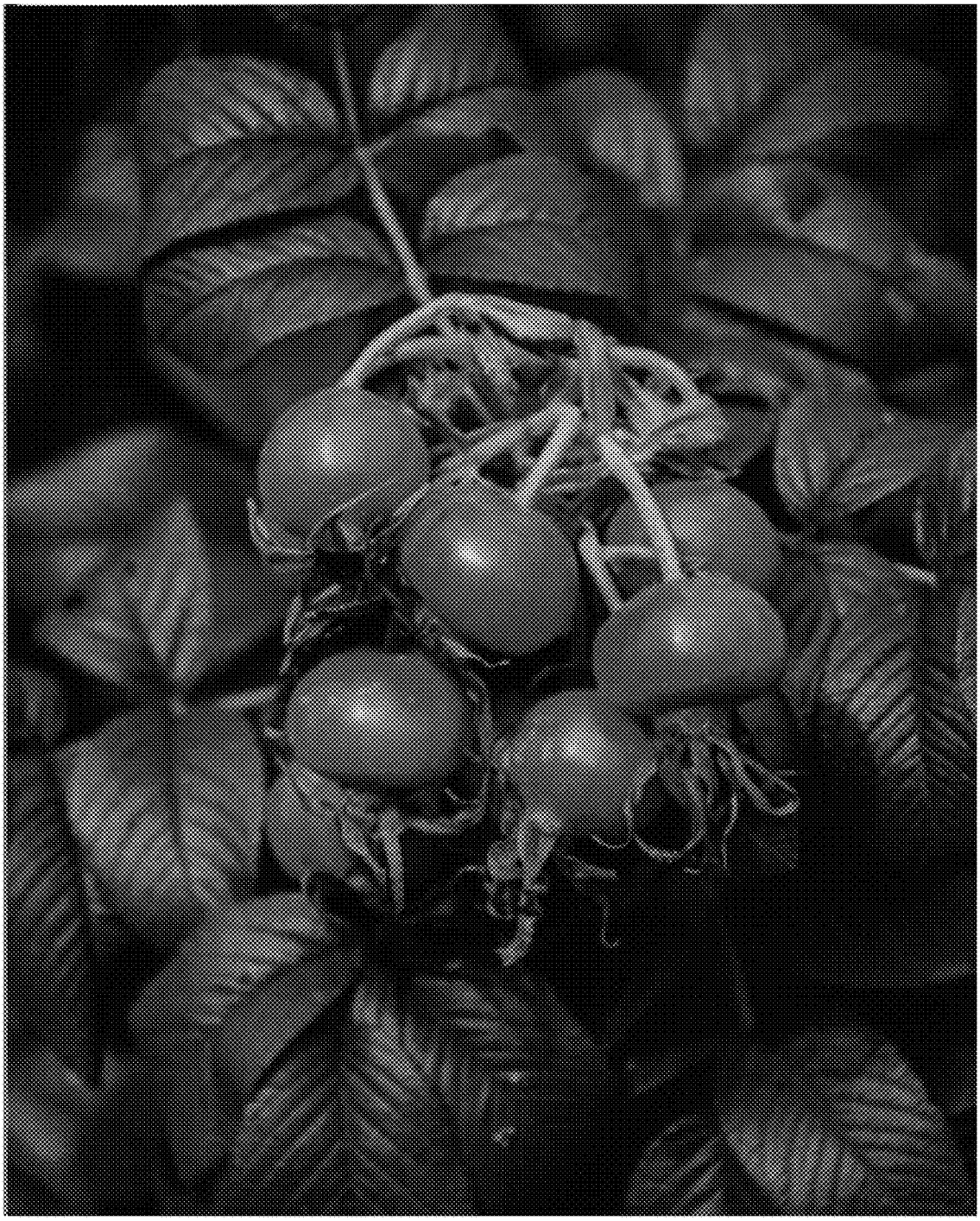

* * * * *